(12) United States Patent
Hanft et al.

(10) Patent No.: US 8,388,607 B2
(45) Date of Patent: Mar. 5, 2013

(54) MULTIPLE-SPOT LASER REFRACTIVE OPHTHALMIC SURGERY

(75) Inventors: Marco Hanft, Jena (DE); Mark Bischoff, Jena (DE); Martin Wiechmann, Jena (DE); Gregory Stobrawa, Jena (DE); Lars Christian Wittig, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 558 days.

(21) Appl. No.: 12/597,720

(22) PCT Filed: Apr. 22, 2008

(86) PCT No.: PCT/EP2008/003221
§ 371 (c)(1), (2), (4) Date: Jan. 13, 2010

(87) PCT Pub. No.: WO2008/131887
PCT Pub. Date: Nov. 6, 2008

(65) Prior Publication Data
US 2010/0137849 A1 Jun. 3, 2010

Related U.S. Application Data
(60) Provisional application No. 60/914,182, filed on Apr. 26, 2007.

(30) Foreign Application Priority Data
Apr. 26, 2007 (DE) .......................... 10 2007 019 812

(51) Int. Cl.
*A61B 18/18* (2006.01)
(52) U.S. Cl. ................... 606/4; 606/5; 606/11

(58) Field of Classification Search ................... 606/3–6, 606/10–13, 16–19
See application file for complete search history.

(56) References Cited

U.S. PATENT DOCUMENTS

| | | | |
|---|---|---|---|
| 4,428,643 A | 1/1984 | Kay | 359/18 |
| 5,152,759 A | 10/1992 | Parel et al. | 606/5 |
| 5,391,165 A * | 2/1995 | Fountain et al. | 606/4 |
| 5,549,632 A * | 8/1996 | Lai | 606/5 |
| 5,631,762 A | 5/1997 | Kataoka | |
| 6,159,202 A * | 12/2000 | Sumiya et al. | 606/4 |
| 6,331,177 B1 | 12/2001 | Munnerlyn et al. | 606/5 |
| 6,376,799 B1 | 4/2002 | Amako et al. | |
| 7,976,155 B2 * | 7/2011 | Muhlhoff et al. | 351/159.02 |
| 2003/0023231 A1 | 1/2003 | Bille | |
| 2006/0287662 A1 | 12/2006 | Berry et al. | |
| 2008/0113493 A1 | 5/2008 | Chall | |
| 2008/0186551 A1 * | 8/2008 | Hanft et al. | 359/205 |

FOREIGN PATENT DOCUMENTS
DE 44 19 038 A1 12/1994
(Continued)

*Primary Examiner* — Mohammed Hasan
(74) *Attorney, Agent, or Firm* — Patterson Thuente Christensen Pedersen, P.A.

(57) ABSTRACT

An apparatus for material processing by laser radiation, including a laser source which emits a processing beam, and a beam path for focusing and scanning, the beam path focusing the processing beam into a processing volume and shifting the position of the focus therein. A beam splitting device generates several foci in the processing volume and the beam splitting device splits the processing beam up into a primary beam and at least one secondary beam and leaves the cross section of the beam in a pupil plane of the beam path unchanged during said division and introduces an angle of separation between the primary and secondary beams, so that these beams expand in the beam path in directions which differ by the angle of separation.

14 Claims, 14 Drawing Sheets

FOREIGN PATENT DOCUMENTS

| | | |
|---|---|---|
| DE | 10 2005 013 949 A1 | 9/2006 |
| DE | 11 2004 002 561 T5 | 10/2006 |
| DE | 602 08 968 T2 | 10/2006 |
| EP | 0 062 545 A1 | 10/1982 |
| EP | 0 402 250 A2 | 12/1990 |
| EP | 1 279 386 A1 | 1/2003 |
| WO | WO 99/53992 | 10/1999 |
| WO | WO 2006/128038 A2 | 11/2006 |

* cited by examiner

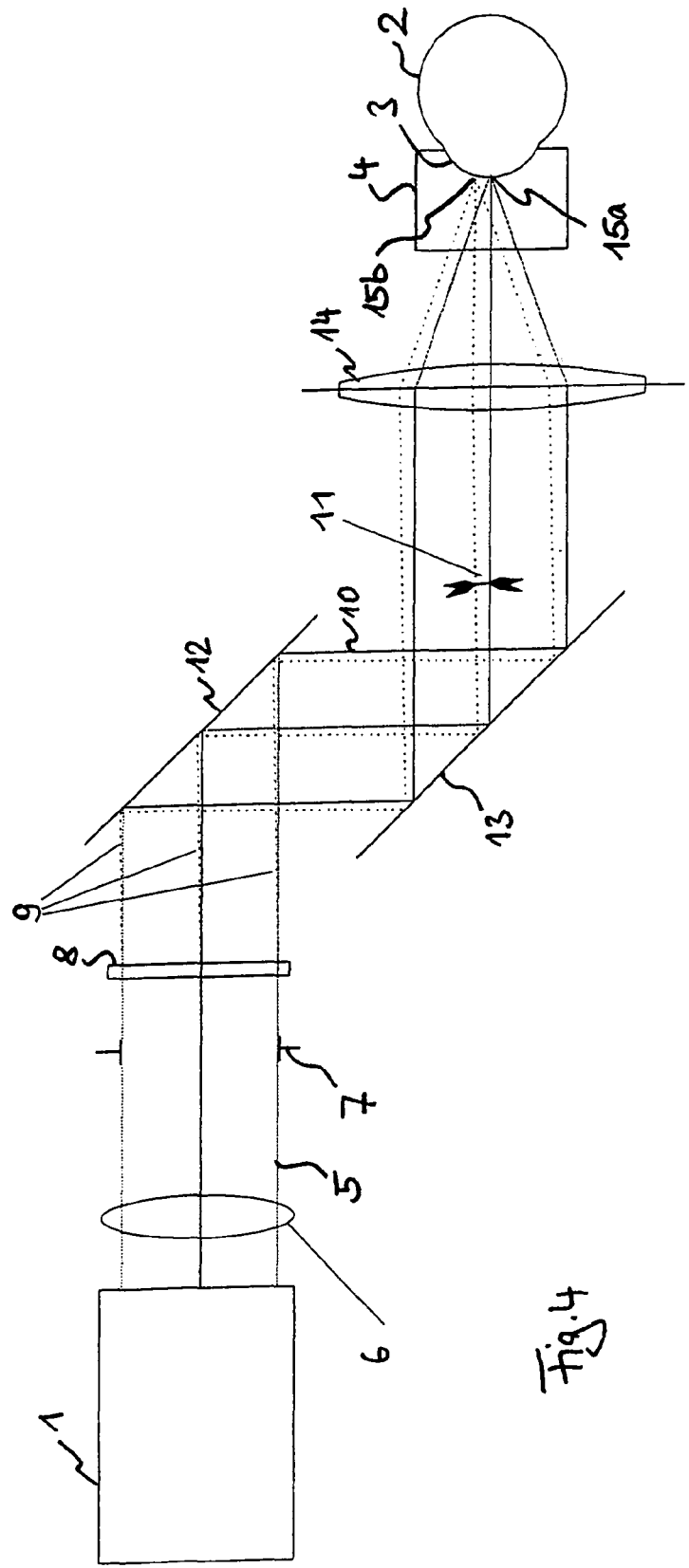

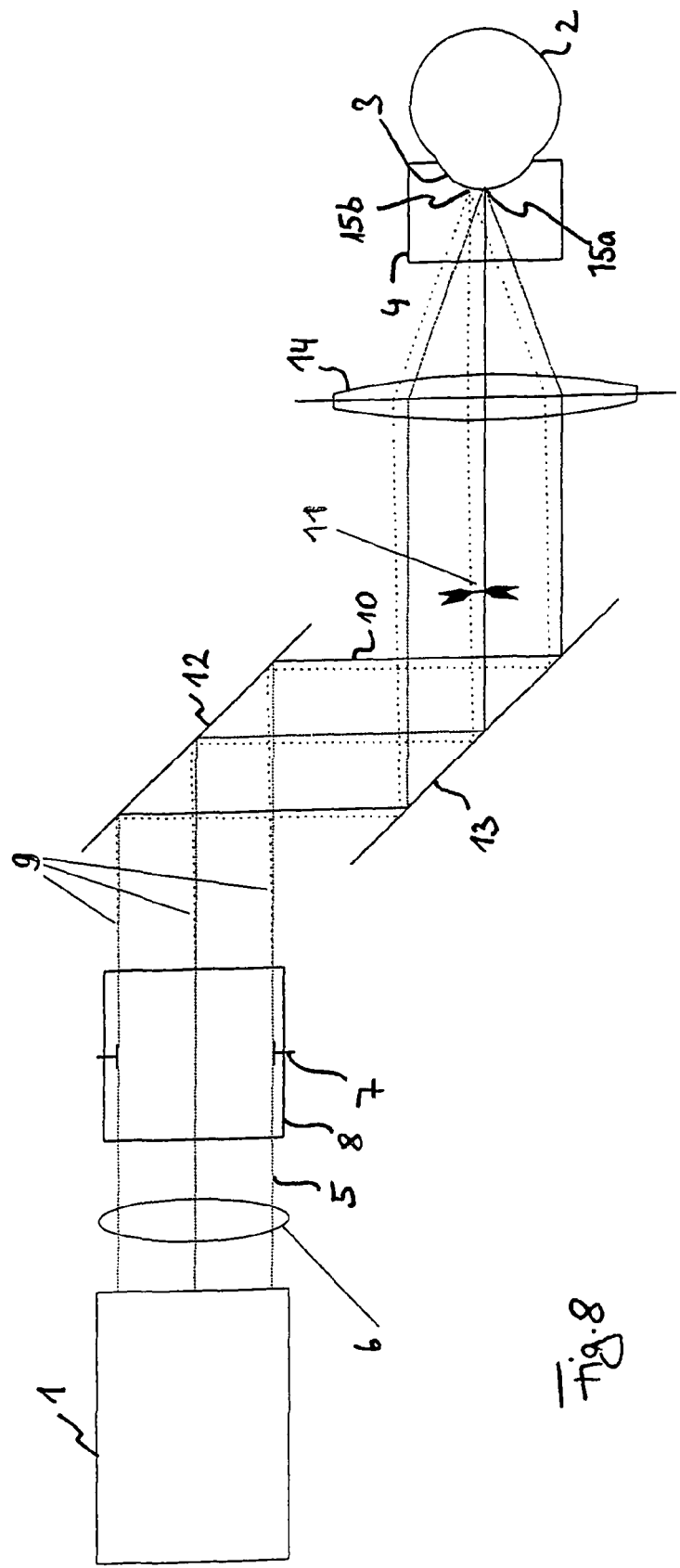

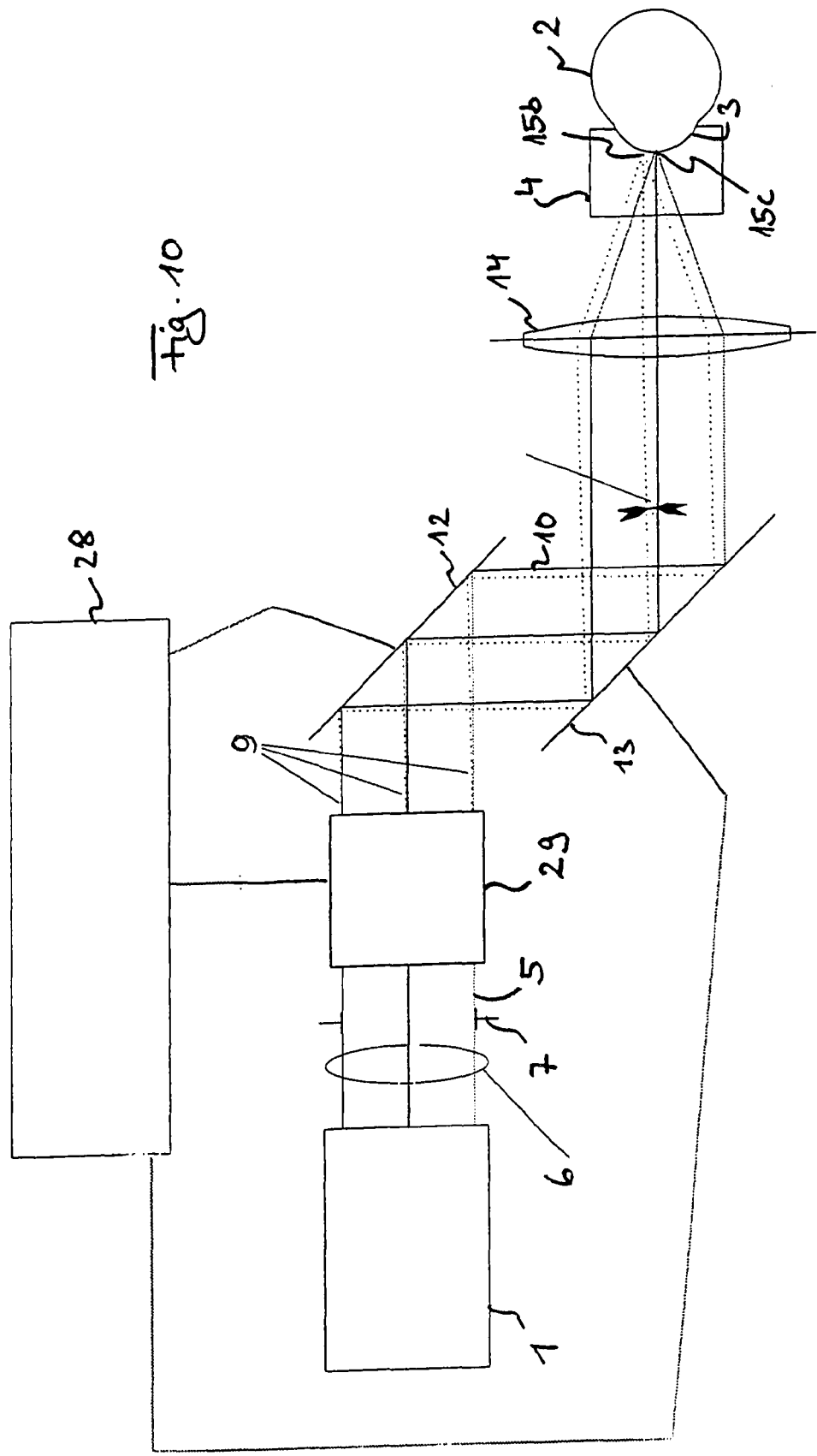

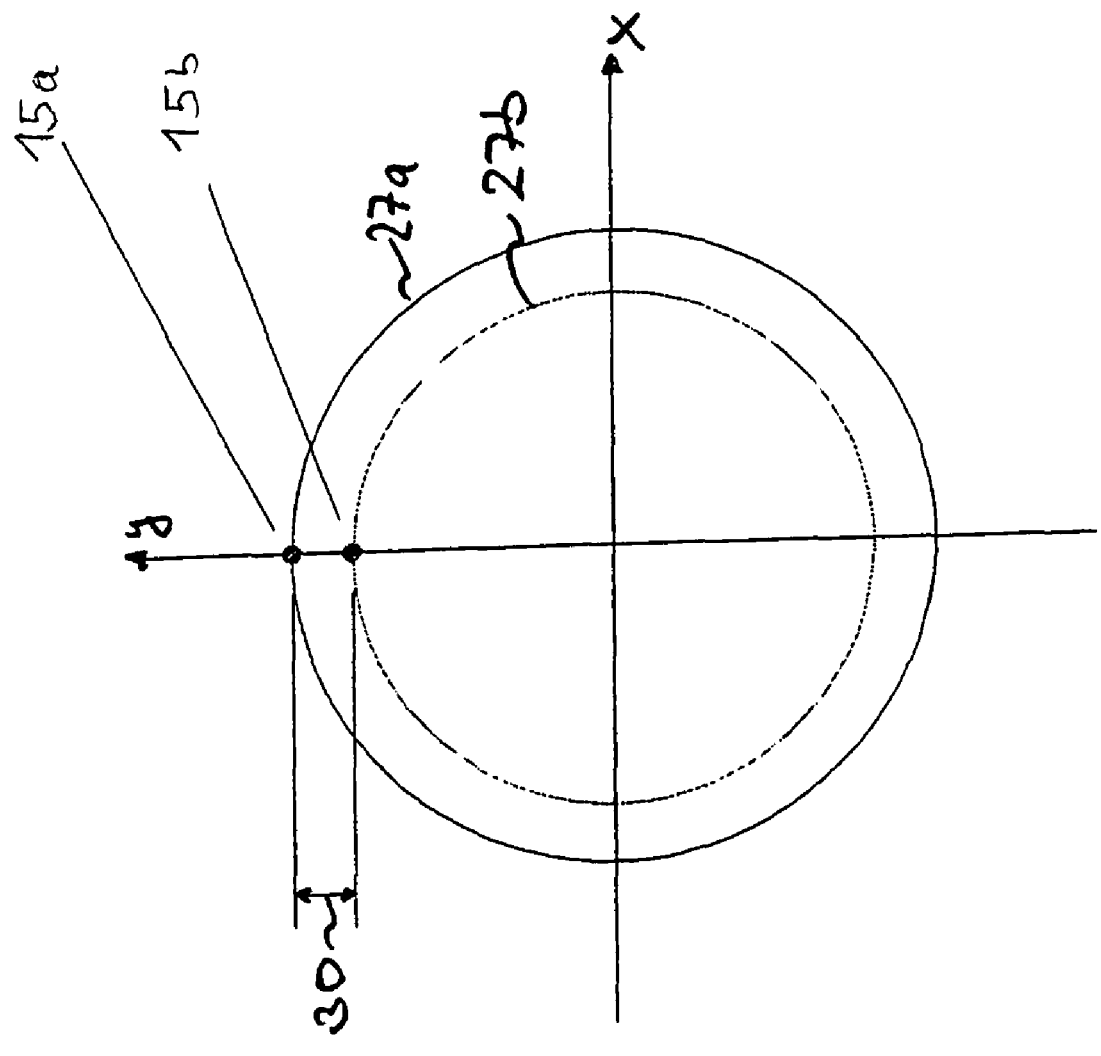

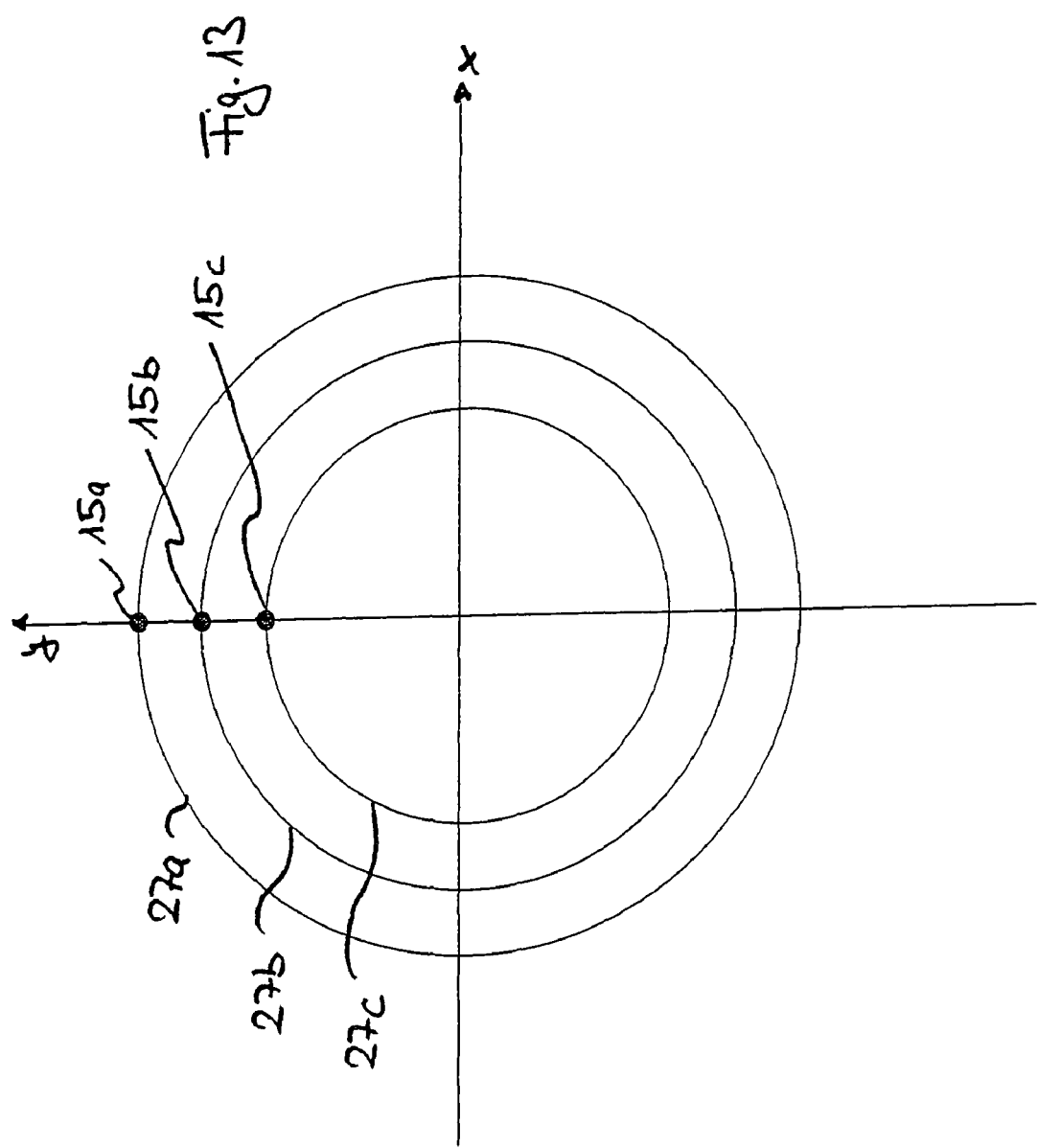

US 8,388,607 B2

MULTIPLE-SPOT LASER REFRACTIVE OPHTHALMIC SURGERY

PRIORITY CLAIM

The present application is a National Phase Entry of PCT Application No. PCT/EP2008/003221, filed Apr. 22, 2008, which claims priority to U.S. Provisional Application No. 60/914,182, filed Apr. 26, 2007, and German Application Number 102007019812.6, filed Apr. 26, 2007, the disclosures of which are hereby incorporated by reference herein in their entirety.

FIELD OF THE INVENTION

The invention relates to an apparatus for refractive ophthalmic surgery by laser radiation, said apparatus comprising a laser source which emits a processing beam, and a beam path for focusing and scanning, said beam path focusing the processing beam into the cornea of an eye and shifting the position of the focus therein, a beam splitting device being provided to generate several foci in the cornea.

BACKGROUND

The processing of material by laser radiation is known. A particular application for processing transparent materials, where a processing effect is obtained by a non-linear interaction of the laser radiation with the per se transparent material, is refractive ophthalmic surgery. For surgery, the laser radiation is focused into the eye's cornea, and the focus is shifted along a cut surface to be generated.

Of course, the processing time depends on how long the interaction in the focus lasts. An acceleration can be achieved by working with several focus spots at a time.

Therefore, EP 1279386 A1, which discloses an apparatus of the above type, describes how to shorten the treatment time by multiplying the spots, allowing the simultaneous processing of larger partial areas. The presented solution has several disadvantages. According to FIG. 4 of this publication, a beam 38 is split into partial beams 44 a . . . c by lenses 42 a . . . c. The diameter the beams 44 a . . . c have directly at the lenses 42 a . . . c is smaller than the diameter of the beam 38. This is a disadvantage, because a smaller beam cross section at the lenses 42 a . . . c causes the beams 44 a . . . c to be have an inferior focusing ability as compared to the beam 38. That is, either larger spots result or the cross sections have to be adapted. After interaction of the near-parallel beam 38 with the lenses 42 a . . . c, convergent beams 44 a . . . c form so that foci are located within the optical system. This is disadvantageous because it may cause high field strengths with undesired effects within the optical system, for example an energy-consuming optical breakthrough at a position in the optical beam path other than the target position in the material to be treated. Moreover, any focusing element always generates a need for adaptation to the subsequent optics, e.g. by collimation. This accordingly results in additional complexity.

Also, in the state of the art, a scanning element is positioned directly in the intermediate image, i.e. conjugated to the actual processing plane. Although the beams would be deflected when using a galvanometer scanner, there would be no change of location. Therefore, the spots would rest in the processing volume despite any deflections of the galvanometer scanner. Further, the design according to DE 60208968 additionally uses an active mirror having 40,000 active facets, which is complex and expensive.

A further problem of the known arrangement is that a fixed offset between the individual spots is generated anterior to the scanner. A spiral scan will then result in points of intersection between the spot paths in the processing volume. This leads to a non-concentric course of the paths, especially for a small number of spots.

SUMMARY OF THE INVENTION

Therefore, it is an object of the invention to provide an apparatus for refractive ophthalmic surgery by laser radiation of the above-mentioned type such that several focus spots can be used without the above-described disadvantages.

According to the invention, this object is achieved by an apparatus for refractive ophthalmic surgery by laser radiation, said apparatus comprising a laser source, which emits a processing beam, and a beam path for focusing and scanning, which beam path focuses the processing beam into the cornea of an eye and shifts the position of the focus therein, a beam splitting device being provided to generate a plurality of foci in the processing volume, which beam splitting device divides the processing beam into primary and secondary beams and leaves the cross section of the beam unchanged during dividing, so that the primary and secondary beams have the same cross section as the processing beam which is incident on the beam splitting device, wherein said beam splitting device introduces an angle of separation between the primary and secondary beams, so that the primary and secondary beams extend in the beam path in directions which differ by the angle of separation, and wherein a contact glass is provided, which induces a predefined geometric interface at the cornea.

It is particularly easy to make the beam splitting device leave the cross section unchanged, preferably in the pupil, if the device itself is located in or near the pupil of the beam path. Further, the beam splitting device preferably does not have a focusing effect. It is also convenient to arrange the beam splitting device anterior to scanning elements in the beam direction.

FIG. 15 shows how the term "closeness to the pupil" is understood in connection with the present invention. It shows an axial beam 40 which is characterized by its peripheral rays 41 and a main ray 42. The aperture of the axial beam 40 is defined by its peripheral rays 41. Further, a field beam 43 is depicted by way of example. A reference plane 44 is located near a pupil plane 45, as long as, for all field beams 43, the intersection point 47 of a main ray 46 and the reference plane 44 is located within the aperture of the axial beam. Thus, a plane's closeness to the pupil is characterized in that the points of intersection where all the field beam main rays pass through the plane are located within the axial beam's aperture which is defined by the peripheral rays.

In order to enable switching between single-spot and multiple-spot processing, it is convenient to provide the effect of the beam splitting device such that it can be switched on and off, for example by a mechanical system which disengages the beam splitting device from the beam path or bypasses it in the beam path.

For splitting, the beam splitting device may comprise a diffractively effective element, which may be provided as a phase grating, for example. Said phase grating preferably also comprises means for distributing the radiation intensity of the incident processing beam as uniformly as possible to a limited number of main maxima.

Particularly uniform distribution of the radiation intensity with the possibility of generating a very great number of secondary beams is possible by the use of a beam splitting device which comprises elements consisting of wedges and planar plates, e.g. in the form of a segmented plate, whose segments alternate between different wedges and planar plate elements.

In the case of circular deflection of the position of the focus in the processing volume, the multiplicity of generated spots may cause intersecting of the respective, e.g. circular, paths on which the foci are shifted. In order to avoid this, it is convenient to control the angle of separation as a function of the target position of the primary spot. A particularly simple realization of this further embodiment is a beam splitting device which rotates the at least one secondary beam about the primary beam in an adjustable manner. For control, an additional further embodiment may then provide a control unit which controls the rotation synchronously with the shifting of the focus position. This prevents intersecting of paths of the spots of the primary and secondary beams. For example, the spots move on concentric circular paths.

It will be appreciated that the features mentioned above and those yet to be explained below can be employed not only in the indicated combinations, but also in other combinations, or alone, without departing from the scope of the present invention.

BRIEF DESCRIPTION OF THE DRAWINGS

The invention will be explained in more detail below, by way of example and with reference to the enclosed drawings, which also disclose features of the invention and wherein:

FIG. 4 depicts a representation similar to FIG. 1 of a particular construction of the beam splitting element;

FIG. 8 depicts a representation similar to FIG. 4, but with a differently designed beam splitting element;

FIG. 10 depicts a treatment apparatus similar to that of FIG. 1, but with a controllable beam splitting element;

FIG. 11 depicts a representation similar to that of FIG. 6 for the treatment apparatus of FIG. 8;

FIG. 13 depicts a representation similar to that of FIG. 6 for a modification of the treatment apparatus of FIG. 10;

DETAILED DESCRIPTION

Figure 1:
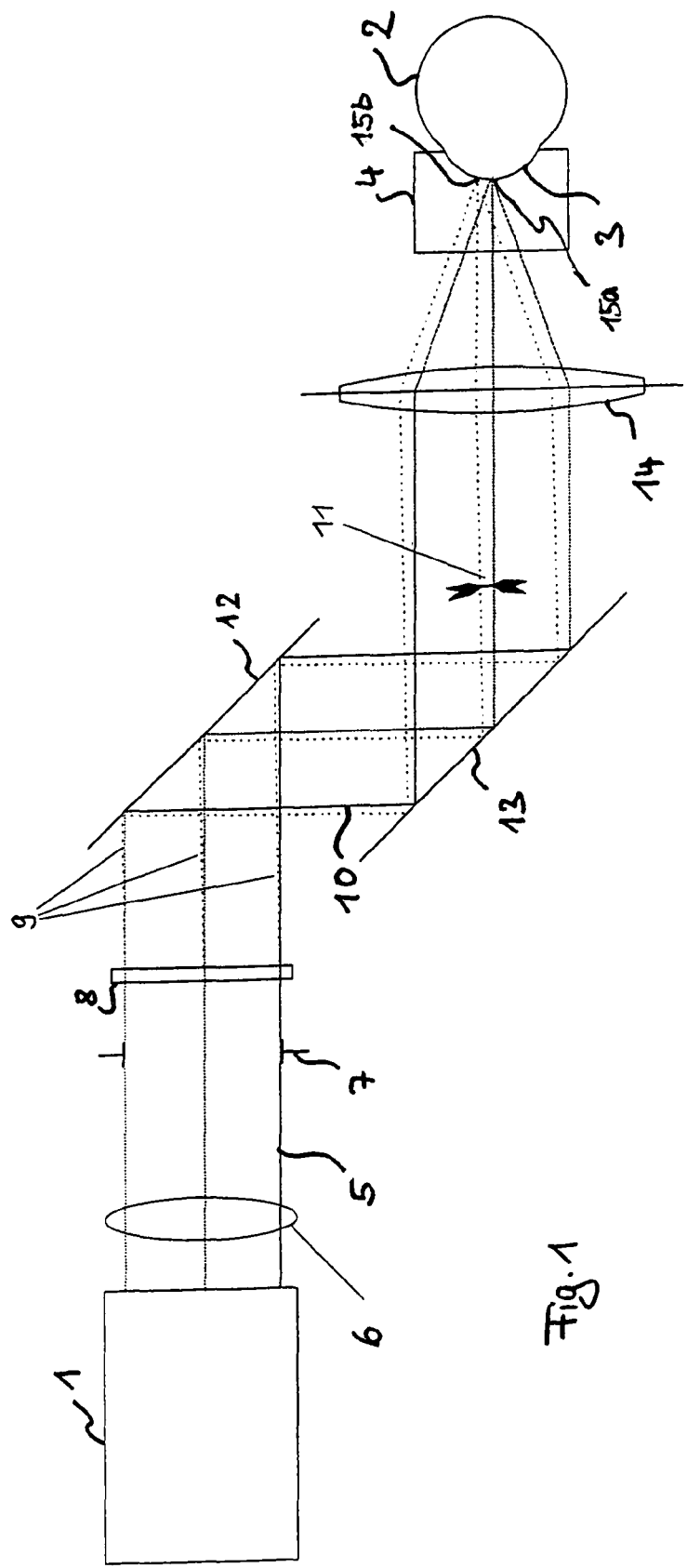
FIG. 1 depicts the beam path for a treatment apparatus using several processing spots.

FIG. 1 shows a laser-surgical system for refraction-correcting treatment of the human eye. The system comprises a source 1 of radiation, which may be provided, for example, as a femtosecond laser, whose radiation is used to process a material, which is the cornea of an eye 2 in the example embodiment described herein. In order to obtain a defined geometrical boundary surface or interface at the cornea 3, a known contact glass 4 is placed on the cornea 3.

The source 1 of radiation provides a processing beam 5, optionally by the use of optics 6 arranged posterior to the source 1 of radiation. An aperture stop 7 defines the cross section of the beam and the pupil in the beam path that leads to the eye 2. Near the aperture stop 7, i.e. near the pupil, there is a beam splitter 8, which divides the incident processing beam 5 such that a secondary beam 9 is split off, which extends in a slightly different direction to that of the primary beam 10 not being split off. The cross section of the processing beam 5 is not changed thereby. The angle of divergence or angle of separation between the primary beam 10 and the secondary beam 9 is indicated by way of example and is referred to by the reference numeral 11. Scanners 12, 13 arranged posterior to the beam splitter 8 deflect the processing radiation in the beam path. Thus, foci 15a, 15b are formed in the processing volume 2 by subsequently arranged focusing optics 14.

Accordingly, the laser-surgical system comprises: a source 1 of radiation (e.g. fs laser), which emits the beam 5; the beam splitter 8, which divides the processing beam into the primary beam 10 and one or more secondary beams 9; one or more scanning elements 12, 13 (for example, scanning mirrors) for deflection of the beams 8, 10; and focusing optics 14, which focus the beams 9, 10 into the cornea 3 of the eye 2.

The source 1 of radiation is preferably a femtosecond laser emitting fs pulses in the wavelength region of 700-1150 nm and over a spectral width of +/−5 nm. The pulse duration is 10-900 fs. Sources of this type are known and may also comprise pulse-shaping devices in addition to the actual laser.

For a multiple focus to form, beam splitting is effected near a pupil. A pupil is an image of an aperture stop 7, or the aperture stop 7 itself. The aperture stop 7 defines the aperture of the beams 5, 9, 10 which opening is used for imaging. The beam splitter 8 generates an angular offset of the secondary beams 9 relative to the primary beam 10. This angle of separation 11 leads to separate foci 15a, 15b in the processing volume posterior to the scanning optics 12, 13, 14. It should be noted here that a great number of alternative positions are possible to locate the beam splitter 8, e.g. on the scanning mirrors 12, 13 themselves, posterior to the scanning mirrors 12, 13 or even as part of the focusing optics 14. The decisive factor is the closeness to the pupil.

The beam splitter 8 deflects portions of the beam 5 into the secondary beams 9. Following the splitter the primary 10 and secondary beams 9 extend in slightly different directions; thus, the angle of separation 11 is formed between the beams 9, 10. The beam splitter 8 further has the property that the beam's cross section remains unchanged. This leads to the particular advantage that the aperture in the foci 15a, 15b remains unchanged and, thus, the size of the foci 15a, 15b does not change. The complexity of an otherwise required adaptation of aperture is dispensed with completely. Also, no additional constructional space is needed apart from the space for the splitter 8.

The beam splitter preferably does not have a focusing effect and, thus, generates no intermediate foci. Thus, undesired effects, such as optical breakthroughs within the system, are avoided.

The scanning elements are preferably galvanometer scanning mirrors 12, 13, which deflect the beam(s) 9, 10 in adjustable directions. Arranged following the scanners 12, 13 are the focusing optics 14 through which the beams 9, 10 are focused into a therapy volume (cornea) 2, where processing is effected. The multiple spots 15a, 15b are guided through the therapy volume by the scanners 12, 13 according to a predetermined path. The predetermined paths are preferably spirals or lines.

Due to the particularly preferable circular paths or circle-like paths (ellipses, spirals), fixed beam splitting produces intersecting of the spot paths, which intersecting can be avoided by closed-loop controlled or synchronized beam splitting, as will be described later.

In order to selectively work without multiplication of the spots, the effect of the beam splitter 8 can be optionally switched off. The beam splitter 8 can be switched on and off in many ways.

Figure 2:
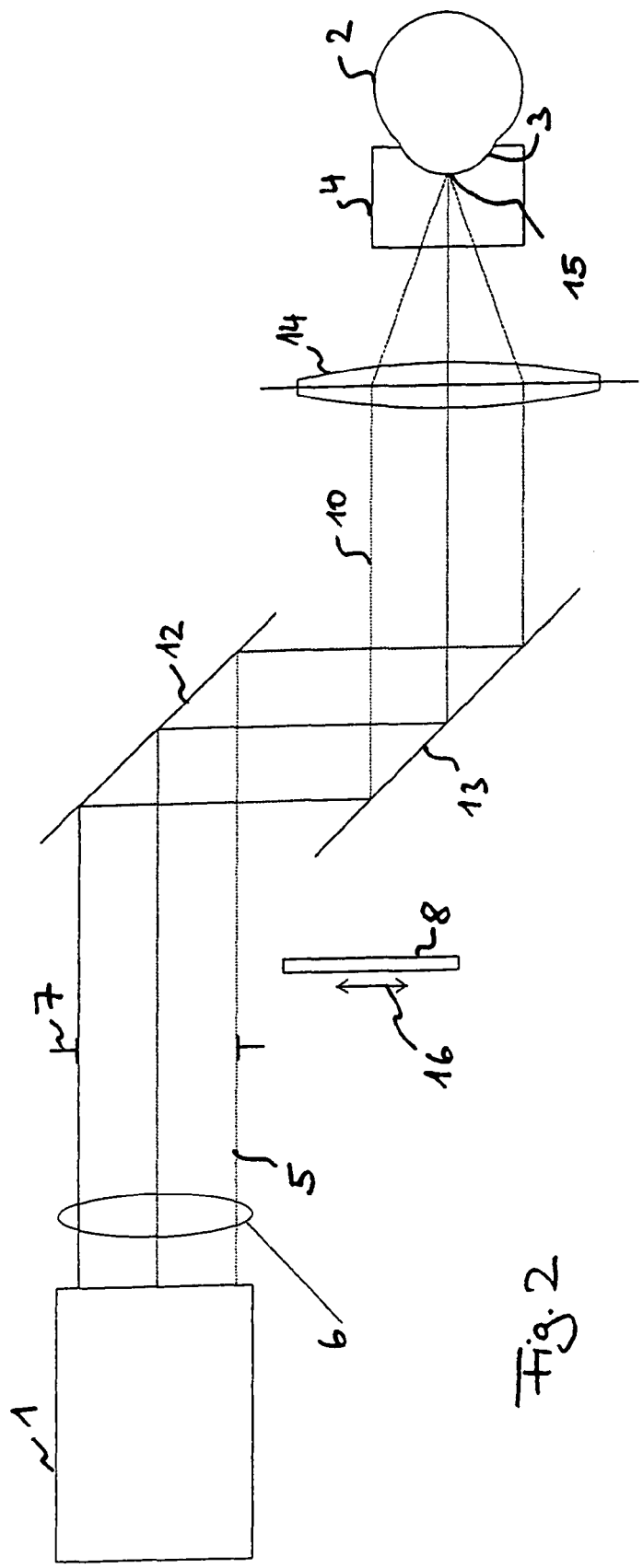
FIG. 2 depicts a further embodiment of the apparatus of FIG. 1.
Figure 3:
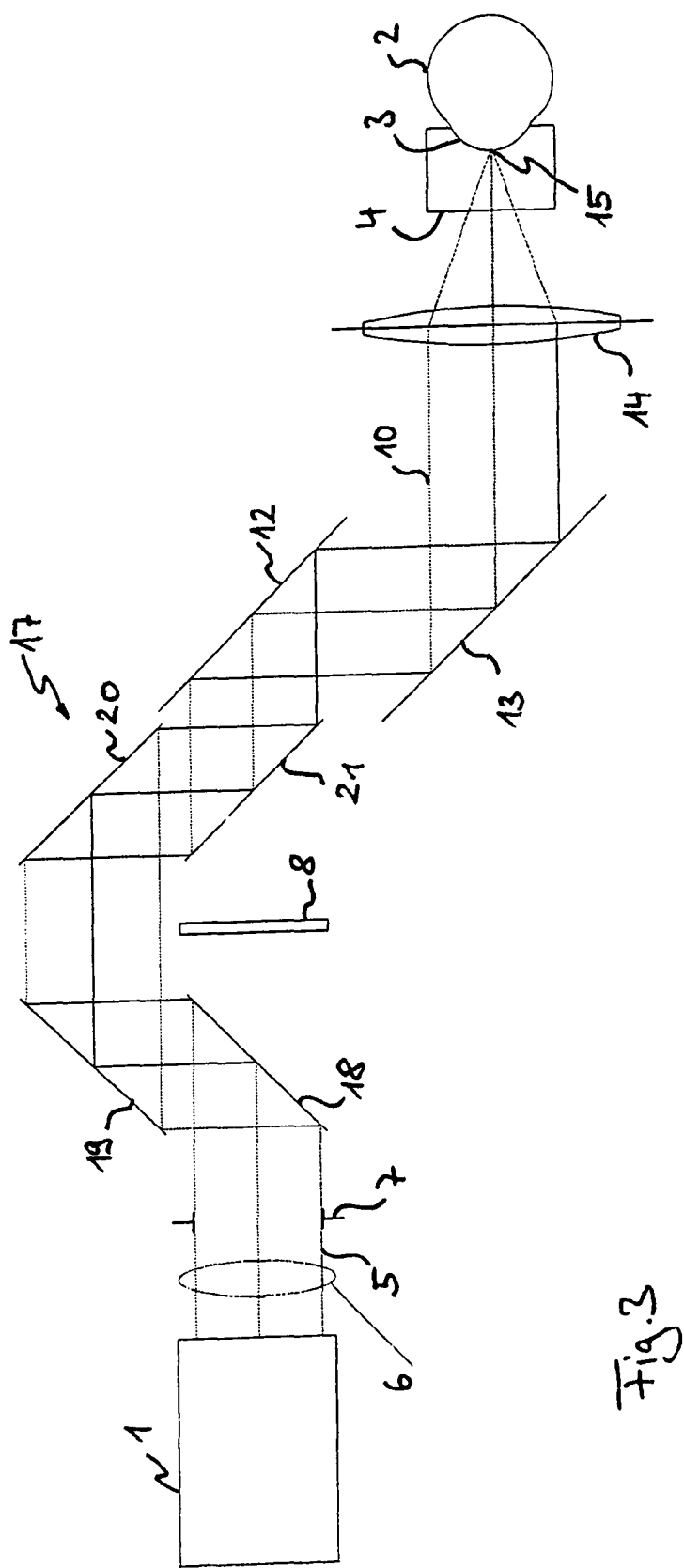
FIG. 3 depicts a further embodiment of the apparatus of FIG. 1.

In FIG. 2 (elements in this and further Figures which correspond to elements already explained are provided with the same reference numerals and shall not be described again), the beam splitter 8 itself is movable, for example. If its effect is desired, it is pushed or folded into the beam path by means of an apparatus. Moreover, it is also possible to bypass the beam splitter 8. A stepped mirror arrangement 17 comprising mirrors 18-21 is provided for this purpose in the example of FIG. 3, said arrangement 17 being movable as a whole or in parts. The mirrors 18 and 21 can be folded in and out of the beam path, for example. When they are folded into the beam path, the stepped mirror arrangement 17 is active and the beam splitter 8 is bypassed. In order to achieve a constant power density per spot in both single-spot operation and multiple-spot operation, the power of the source 1 of radiation is preferably adapted to the status of the beam splitter 8 (active or deactivated).

A diffractively working element (grating) is preferred for the beam splitter 8. Referring to FIG. 4, a phase grating is explained as an example of a specific set of parameters, for ease of illustration. It is expressly pointed out that similar solutions can be embodied also using other gratings and other sets of parameters. In the construction of FIG. 4, the aperture stop has a diameter of 15 mm. The phase grating has a period of 4.16 mm. This leads to an angle of separation of 0.014°. The focal length of the focusing optics is 20 mm. A possible design of the phase grating of the beam splitter 8 and its function are explained hereinafter with reference to FIGS. 5a-c.

The beam splitter 8 is a binary phase grating, which leads to beam splitting in different directions according to the grating formula:

$$\sin\alpha = \pm k\frac{\lambda}{g}$$

with $\alpha$ being the direction of the maxima, k being orders, $\lambda$ being the wavelength and g being the grating constant.

The separation between the foci is obtained approximately according to $$y' = f \cdot \tan\alpha \approx f \cdot \sin\alpha$$

with y' being the focus position for the $0^{th}$ order, $\alpha$ being the direction of the maxima and f being the focal length of the focusing optics.

Figure 5A:
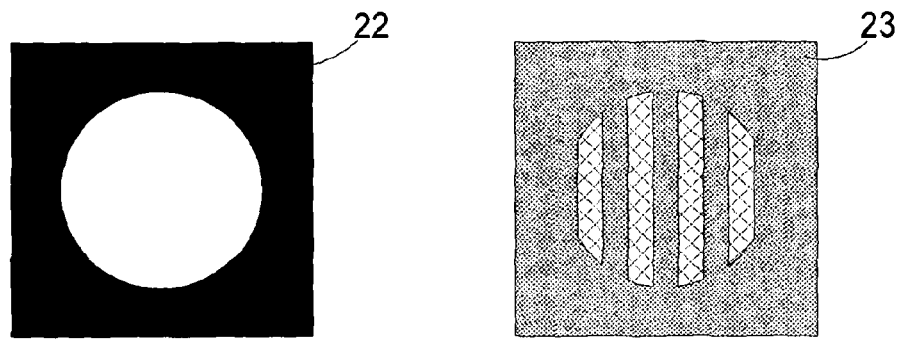
FIGS. 5a-c depict representations explaining the construction and function of the beam splitting element of FIG. 4.
Figure 5B:
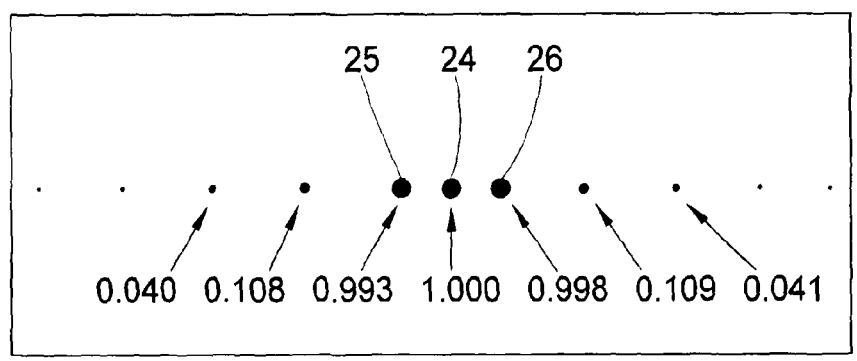
Figure 5C:
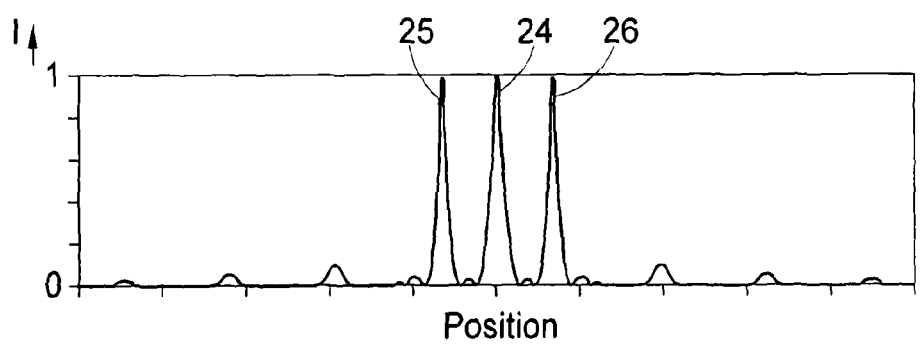

For a wavelength of, for example, 1040 nm, the $+/-1^{th}$ orders are at +/-0.014 degrees relative to the $0^{th}$ order. Thus, posterior to the focusing optics, which have a focal length of 20 mm, a deviation of 5 μm results between the foci. Due to a preferably provided groove shape of the grating, the major part of the energy is diffracted into the $0^{th}$, the $-1^{th}$ and the $+1^{th}$ order. The differences in intensity between the three main maxima are minimal. Of course, other means are also possible for this purpose. If the threshold for the optical breakthrough is, for example, at 30% of the maximum intensity, only the 3 main maxima will produce an optical breakthrough. Thus, the beam has been tripled. FIGS. 5a-c show the pupil function and the intensity distribution of a binary phase grating having a period of 4.16 mm, a bar-space-ratio of 1:1, a phase amplitude of 2.015 rad and a symmetric arrangement.

FIG. 5a shows the pupil function for the grating in the form of an amplitude image 22 as well as a phase image 23. The diffraction characteristics of this grating are illustrated in FIGS. 5b and 5c. As can be seen, the main energy flows into the $0^{th}$ order 24 as well as the $+1^{th}$ order 25 and as the $-1^{th}$ order 26. FIG. 5b shows the intensity values as the peak intensity for each order, normalized to the peak intensity of the $0^{th}$ order. The plotting of the intensity I in FIG. 5c also illustrates that only the first three main maxima carry radiation sufficient for an optical breakthrough. Integral evaluation of the peaks shows that a mere 16.35% of the radiation energy passes into still higher orders of diffraction ($2^{nd}$ orders and above) and is, thus, not available. Accordingly, the phase grating effectively achieves splitting of the processing beam 5 into a primary beam 24 (corresponding to the $0^{th}$ order) as well as two secondary beams 25, 26 (corresponding to the $+/-1^{th}$ orders).

Figure 6:
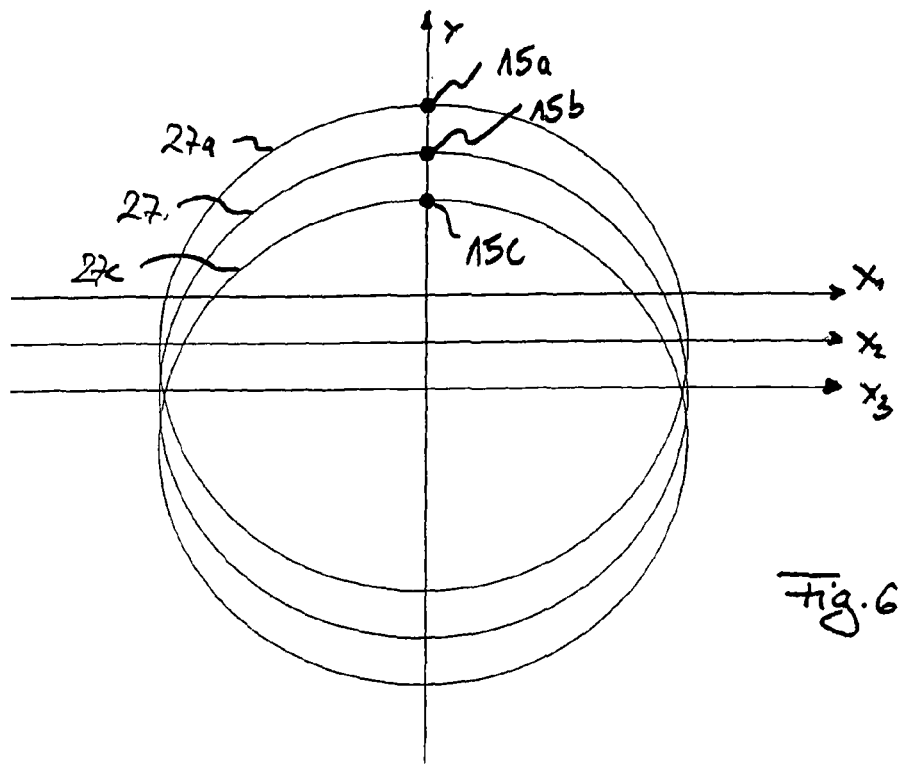
FIG. 6 depicts paths of the multiple-spot foci generated in the processing volume by the treatment apparatus of FIG. 4.

In the described embodiments, the beam splitter anterior to the scanning mirrors 12, 13 causes a fixed offset, e.g. in the y direction. If the scanners 12, 13 are controlled according to a circular path for the $0^{th}$ order, the image of FIG. 6 will result in the target volume. The foci 15a, 15b move along circular paths 27a, b, c whose centers are mutually offset.

In the case of such a fixed offset, a grating design is of advantage which two-dimensionally generates more than 3 foci. This can be achieved, for example, in that the primary beam is divided by the beam splitter 8 in two spatial directions. Said splitting may be effected by sequential splitting in two directions, which are preferably orthogonal to one another, as achieved, for example, by an arrangement of two diffraction gratings, which are rotated relative to each other at 90° about the beam axis. Since these two diffractive elements are to be arranged at least approximately in a position in the beam path that is optimal for splitting (pupil or near the pupil), an arrangement of the two in immediate spatial proximity to one another is preferred.

Figure 7:
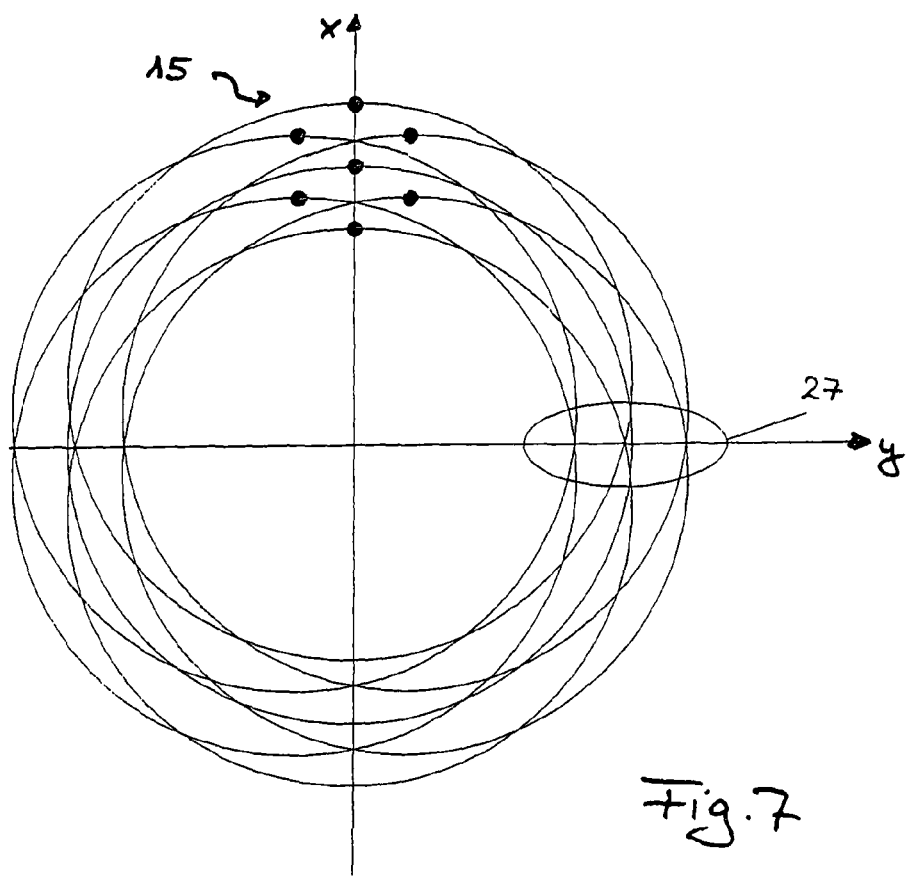
FIG. 7 depicts a representation similar to FIG. 6 for seven spots.

The focus image of an arrangement comprising 7 spots is schematically shown as an example in FIG. 7. The individual spot paths 27 intersect several times, forming a ring-like pattern. The Figure shows the spot paths 27, with the intersection of the spot paths 27 resulting from the fixed splitting being clearly visible. The unfavorable effects of an intersection can be reduced by greater distances between the individual spots 25, bearing in mind, however, that all spots are located in one plane perpendicular to the optical axis. This prerequisite has to be taken into account when defining the separation distance. If two-dimensionally curved cut surfaces (e.g. spheres) are to be cut, this will result in an upper limit for the separation distance. In the case of a spherical cut having a radius of curvature of 20 mm, the strictest criterion occurs for points which are remote from the center. Depending on the definition of the depth tolerance, a specific distance from the center (e.g. 5 mm) will yield a maximum allowable separation distance (of the group of spots generated, i.e. a sort of diameter of the group of spots). This distance is, for example, 3 μm for a depth tolerance of 0.8 μm, approximately 5 μm for a depth tolerance of 1.3 μm, or 10 μm for a depth tolerance of 2.6 µm. A limitation to, for example, few µm in the diameter of the group of spots appears useful for applications.

In a further embodiment according to FIGS. 8 and 9 *a-c*, a segmented element whose segments consist of glass strips is used as the beam splitter 8. The strips are provided as wedges A and C or as a planar plate B. An example is specifically dimensioned here. However, it is expressly pointed out that other sets of parameters also yield valuable solutions. Such sets can be found by a person skilled in the art by modifying the parameters explained below. FIG. 8 shows only the beams of segments A and B.

Figure 9C:
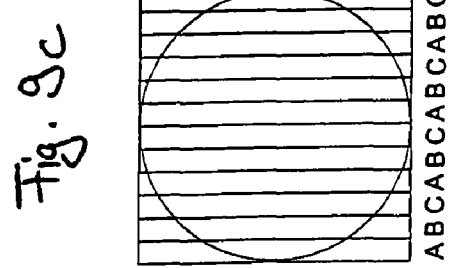
FIGS. 9a-c depict representations explaining the construction of the beam splitting elements of FIG. 8.
Figure 9B:
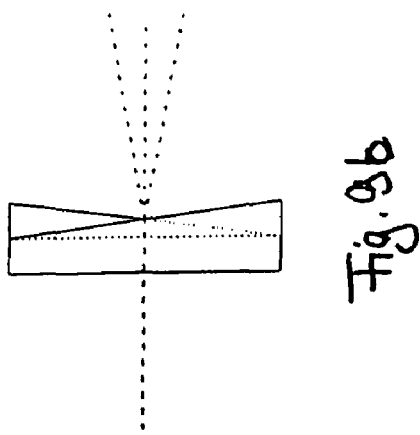
Figure 9A:
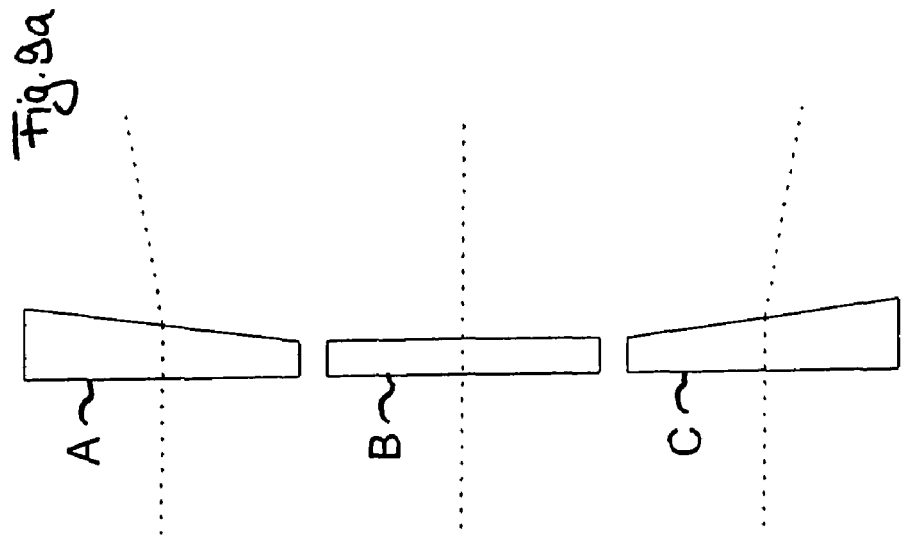

Each wedge A, C deflects a beam. For scanning optics having a focal length of 20 mm and a distance of 5 µm between the spots, an angle of separation of 0.014° results. This angle is formed by wedges having a refractive index of n=1.5 and a wedge angle of 1.72 angular minutes. In order to provide 3 beams (−0.014°/0°/+0.014°), the pupil can be divided. For this purpose, wedge segments and segments of planar plates are combined, as shown in FIGS. 9 *a, b, c*, which depict lateral views of the individual elements (FIG. 9*a*) of the segmented element (FIG. 9*b*) and a top view of the segmented element (FIG. 9*c*).

The above-explained variants with fixed beam splitting generate a deflection anterior to the scanners 12, 13. This deflection is fixed and causes a fixed offset. In this case, each spot 15 for itself may move on a circular path, but the circular paths are not concentric. In order to avoid this, a manipulator unit realizes controlled beam splitting according to a further embodiment. In this case, beam splitting is effected depending on control signals from a control unit 28. Said control unit 28 realizes a synchronization between the scanners 12, 13 and a manipulator unit 29 for the beam splitter 8, as shown in FIG. 10.

Offset control is effected as a function of the target position of the primary spot and enables, for example, a spiral scan without the paths intersecting. The primary and secondary spots 15*a*, 15*b* move on concentric circular paths 27*a*, 27*b* having a fixed path distance 30, as shown in FIG. 11.

Figure 12A:
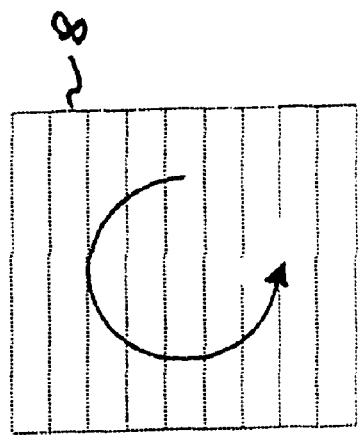
FIGS. 12a-b depict drawings relating to the construction and function of the beam splitting element of FIG. 10.
Figure 12B:
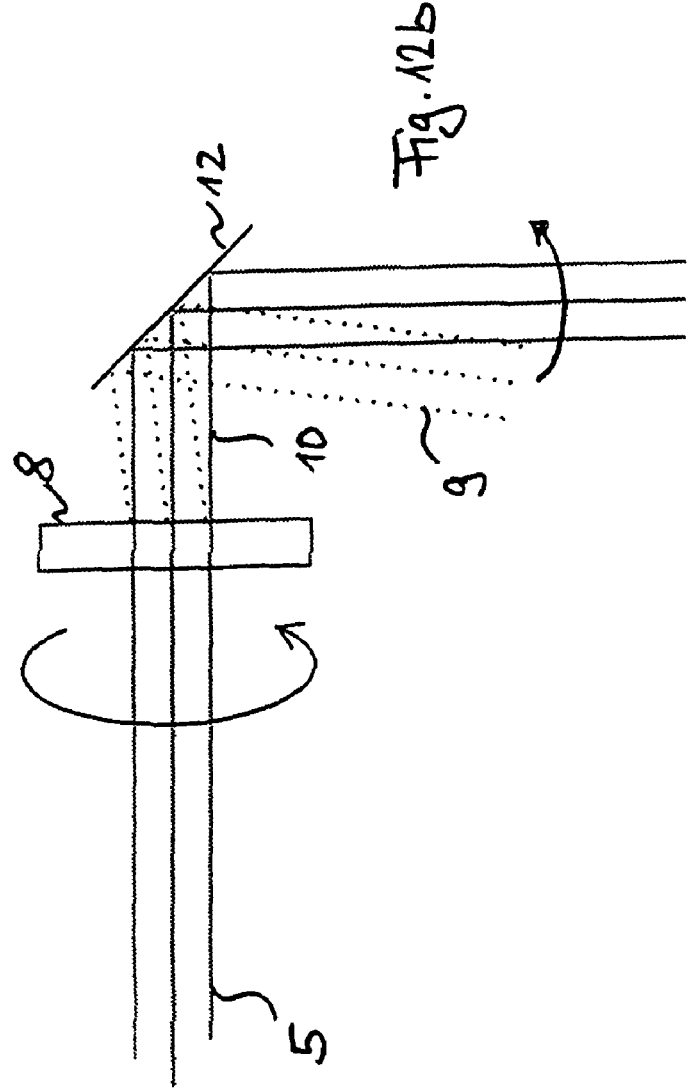

The manipulator may preferably be provided as a rotary beam splitter 8 according to FIGS. 12 *a, b*. As described above, the beam splitter 8 may be a phase grating or a segmented plate. The rotation of the beam splitter 8 is synchronized with the x and y control of the scanners by the control unit, so that, as a result, the secondary beams 9 rotate around the primary beam 10.

If the beam is split into three parts (e.g. by the phase grating or the element consisting of wedge segments) and appropriately synchronized, the spots will move concentrically (FIG. 13).

Figure 14:
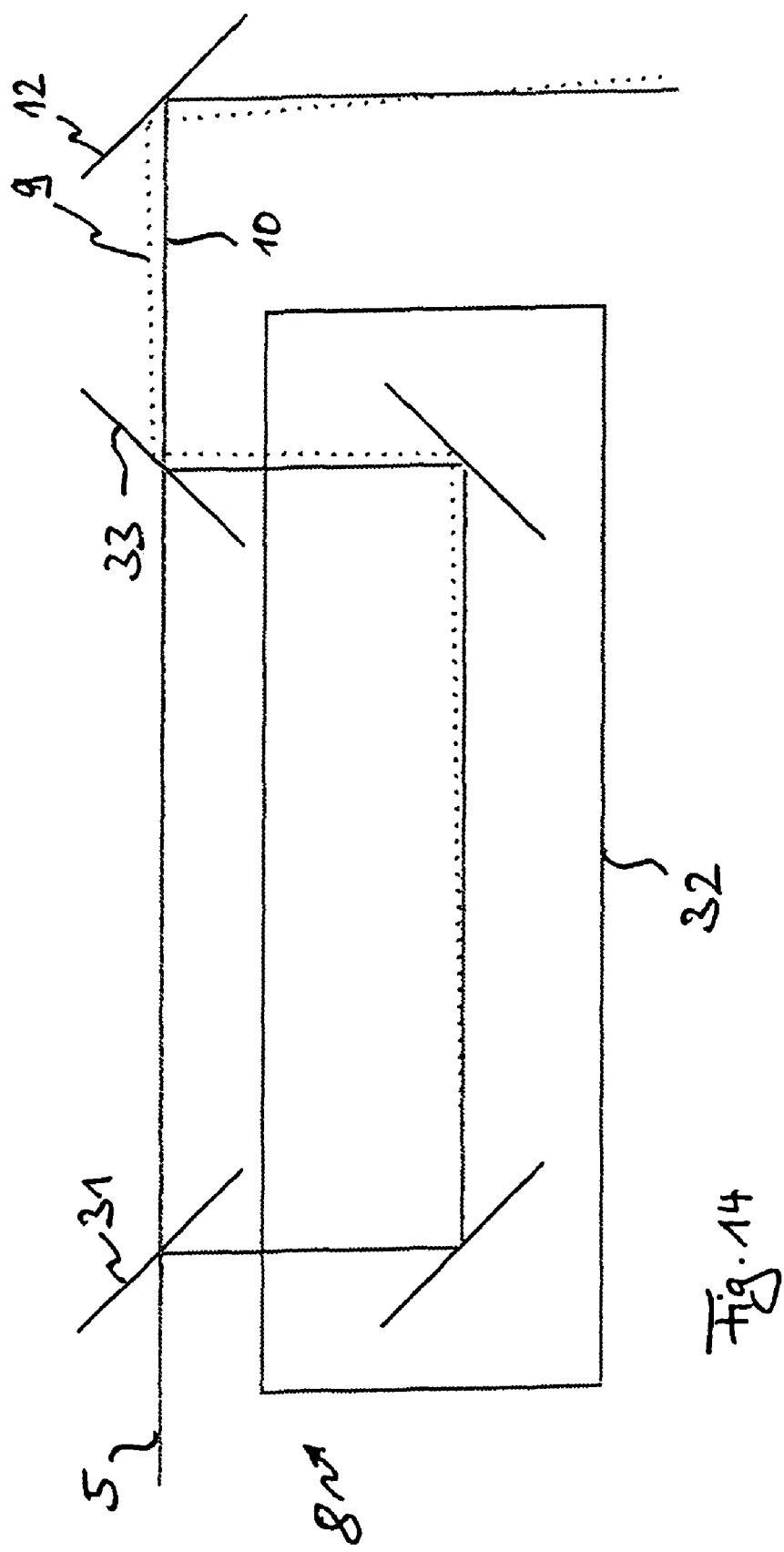
FIG. 14 depicts a schematic drawing of a further beam splitting element for a treatment apparatus with analogy to FIG. 1.
Figure 15:
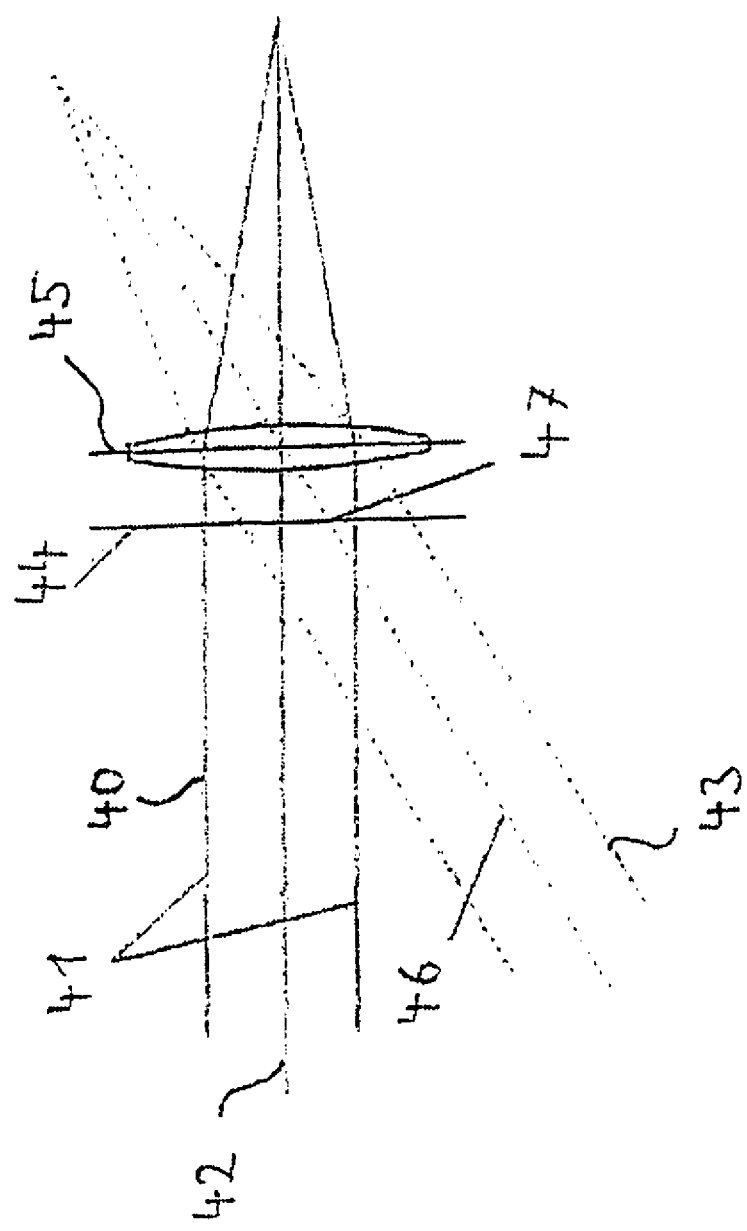
FIG. 15 depicts a schematic drawing explaining the term "proximity to the pupil".

In a further embodiment for a manipulator unit 32 according to FIG. 14, manipulation of the secondary beam 9 is effected separately. The primary beam 10 passes through the beam splitter 8 without manipulation. A splitter 31 separates a part of the processing beam, said part forming the secondary beam 9 which is subjected to manipulation (offset) in unit 32. The secondary beam 9 then gets the primary beam 10 superimposed by means of a further splitter 33. Utilizing polarization allows to optimize separation and superimposing with negligible losses. Two foci are generated. This variant is realizable in a fixed manner and in a controlled or synchronized manner.

The manipulator in unit 32 can be embodied in many ways, e.g. as a mirror (stationary or scanning), a rotary wedge and/or a pair of wedges which are rotated relative to each other for offset adjustment.

The invention claimed is:

1. An apparatus for refractive ophthalmic surgery by laser radiation, said apparatus comprising:
    a source of radiation which emits a processing beam;
    a beam path for focusing and scanning, said beam path focusing the processing beam into a cornea of an eye and shifting a position of a focus therein;
    a beam splitting device that generates several foci in the cornea, wherein the beam splitting device divides the processing beam into a primary beam and at least one secondary beam and leaves a cross section of the beam unchanged during said division, so that the primary and secondary beams have the same cross section as the processing beam which is incident on the beam splitting device;
    wherein the beam-splitting device introduces an angle of separation between the primary and secondary beams, so that the primary and secondary beams expand in the beam path in directions which differ by the angle of separation; and
    further comprising a contact glass which induces a predefined geometric boundary surface at the cornea.

2. The apparatus as claimed in claim 1, wherein the beam splitting device does not have a focusing effect.

3. The apparatus as claimed in claim 1, wherein the beam splitting device is arranged close to a pupil in the beam path.

4. The apparatus as claimed in claim 1, wherein the beam splitting device is arranged anterior to scanning elements.

5. The apparatus as claimed in claim 1, wherein the beam splitting device can be activated and de-activated.

6. The apparatus as claimed in claim 1, wherein the beam splitting device comprises a diffractively working element.

7. The apparatus as claimed in claim 6, wherein said element is a phase grating.

8. The apparatus as claimed in claim 1, wherein the beam splitting device comprises an element which comprises wedges and planar plates.

9. The apparatus as claimed in claim 1, wherein the beam splitting device rotates the at least one secondary beam around the primary beam.

10. The apparatus as claimed in claim 9, further comprising a control unit, which controls the rotation synchronously with the focus position adjustment.

11. The apparatus as claimed in claim 10, wherein the beam splitting device comprises a rotating grating or a rotating segmented plate.

12. The apparatus as claimed in claim 10, wherein the beam splitting device separately directs the at least one secondary beam to a scanning device which deflects the at least one secondary beam in a controlled manner before the beam splitting device superimposes the primary beam again on the thus-deflected at least one secondary beam.

13. The apparatus as claimed in claim 9, wherein the beam splitting device comprises a rotating grating or a rotating segmented plate.

14. The apparatus as claimed in claim 9, wherein the beam splitting device separately directs the at least one secondary beam to a scanning device which deflects the at least one secondary beam in a controlled manner before the beam splitting device superimposes the primary beam again on the thus-deflected at least one secondary beam.

* * * * *

UNITED STATES PATENT AND TRADEMARK OFFICE
CERTIFICATE OF CORRECTION

PATENT NO. : 8,388,607 B2  
APPLICATION NO. : 12/597720  
DATED : March 5, 2013  
INVENTOR(S) : Marco Hanft et al.

Page 1 of 1

It is certified that error appears in the above-identified patent and that said Letters Patent is hereby corrected as shown below:

On the Title page of patent under (75) Inventors: delete "Gregory" and insert --Gregor--

Signed and Sealed this  
Thirteenth Day of August, 2013

Teresa Stanek Rea  
*Acting Director of the United States Patent and Trademark Office*